(12) United States Patent
Forrester et al.

(10) Patent No.: US 10,206,962 B1
(45) Date of Patent: *Feb. 19, 2019

(54) METHOD FOR TREATING FUNGAL INFECTIONS IN NAILS

(71) Applicant: Marlinz Pharma, LLC, Houston, TX (US)

(72) Inventors: Perry Forrester, Houston, TX (US); Joshua Scott, Houston, TX (US); James Adkinson, Clermont, FL (US)

(73) Assignee: Marlinz Pharma, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,732

(22) Filed: Aug. 8, 2017

Related U.S. Application Data

(60) Provisional application No. 62/372,132, filed on Aug. 8, 2016.

(51) Int. Cl.
| | |
|---|---|
| *A61K 36/185* | (2006.01) |
| *A61K 31/045* | (2006.01) |
| *A61K 31/047* | (2006.01) |
| *A61K 31/17* | (2006.01) |
| *A61K 31/19* | (2006.01) |
| *A61K 31/201* | (2006.01) |
| *A61K 31/22* | (2006.01) |
| *A61K 31/23* | (2006.01) |
| *A61K 31/325* | (2006.01) |
| *A61K 31/34* | (2006.01) |
| *A61K 31/355* | (2006.01) |

(52) U.S. Cl.
CPC .......... *A61K 36/185* (2013.01); *A61K 31/045* (2013.01); *A61K 31/047* (2013.01); *A61K 31/17* (2013.01); *A61K 31/19* (2013.01); *A61K 31/201* (2013.01); *A61K 31/22* (2013.01); *A61K 31/23* (2013.01); *A61K 31/325* (2013.01); *A61K 31/34* (2013.01); *A61K 31/355* (2013.01)

(58) Field of Classification Search
None
See application file for complete search history.

(56) References Cited

U.S. PATENT DOCUMENTS

| | | | |
|---|---|---|---|
| 4,810,498 | A | 3/1989 | DiMeglio |
| 5,519,059 | A | 5/1996 | Sawaya |
| 5,525,635 | A | 6/1996 | Moberg |
| 6,391,879 | B1 | 5/2002 | Reeves |
| 7,074,392 | B1 | 7/2006 | Friedman |
| 7,374,772 | B2 | 5/2008 | Bommarito |
| 8,333,981 | B2 | 12/2012 | Trimble |
| 8,952,070 | B2 | 2/2015 | Lindahl |
| 8,987,330 | B2 | 3/2015 | Karlsson |
| 9,561,279 | B2 | 2/2017 | Lindahl |
| 9,782,372 | B2 | 10/2017 | Karlsson |
| 2011/0207765 | A1 | 8/2011 | Van Den Bussche |
| 2012/0010227 | A1 | 1/2012 | Lusiana |
| 2012/0129942 | A1 | 5/2012 | Lindahl |
| 2015/0306052 | A1 | 10/2015 | Karlsson |
| 2017/0258917 | A1 | 9/2017 | Lindahl |

OTHER PUBLICATIONS

Fungifoam® (NDC 49406-004). (Year: 2012).*
Home Health® Antifungal Lotion. (Year: 2009).*
Crawford, et al., Topical Treaments for Fungal Infections of the Skin and Nails of the Foot, The Cochrane Collaboration, 1999, Issue 3.
podiatrynetwork.com, Topical Treatment for Fungal Toenails, www.podiatrynetwork.com/document_disorders.cfm?id=313, accessed Jul. 14, 2016.
Faergemann, et al., Early and Visible Improvements after Application K101 in the Appearance of Nails . . . , J. of Cosmetics, 2011, 1, 59-63.

* cited by examiner

*Primary Examiner* — Michael Barker
(74) *Attorney, Agent, or Firm* — Bushman Werner, P.C.

(57) ABSTRACT

A method of treating nail diseases by topically applying to the nails a composition containing undecylenic acid and tolnaftate, a urea-based component, a monohydric alcohol such as isopropanol, a diol such as propylene glycol, dimethyl isosorbide, and a carboxylic acid, preferably lactic acid.

14 Claims, No Drawings

METHOD FOR TREATING FUNGAL INFECTIONS IN NAILS

CROSS REFERENCE TO RELATED APPLICATION

This application claims priority to U.S. Application No. 62/372,132 filed on Aug. 8, 2016, the disclosure of which is incorporated herein by reference for all purposes.

FIELD OF THE INVENTION

The present invention relates to a method for the topical treatment of nails, e.g., finger nails and toe nails. More particularly, the present invention relates to a method for treating nails and surrounding tissue affected by or susceptible to infections, e.g., fungal infections.

BACKGROUND OF THE INVENTION

The prior art abounds with compositions used to treat nails of an individual for cosmetics purposes, therapeutic purposes, preventative purposes, or all of the above. In particular, fungal infections of various types of the nails, particularly toe nails, are common and there are numerous, commercially available topical preparations to treat these fungal infections.

One disadvantage of many commercially available compositions for treating nail fungal infections, be they over-the-counter or proprietary, is that the compositions typically contain a large proportion of oil. Thus, the prior art compositions typically contain oils, principally of vegetable origin, which are also used in a wide variety of cosmetic products. As is known, these cosmetic oils are composed principally of saponifiable esters, particularly fatty acid tryglycerides. Non-limiting examples of such vegetable oils include soybean oil, avocado oil, corn oil, sesame oil, sunflower oil, almond oil, etc. It is also known to use oils and fats derived from animals such as mink oil, and beef tallow.

Antifungal compositions containing a high proportion of oils and fats, be they vegetable or animal, suffer from several disadvantages. For one, because these oils are prone to degradation, the compositions typically contain a preservative or antioxidant as for example parabens, i.e., esters of parahydroxybenzoic acid, the most common being methyl paraben, propyl paraben, and butyl paraben. In addition, antioxidants such as butylated hydroxyanisole (BHA) and butylated hydroxytoluene (BHT) have also been used as preservatives/antioxidants. While there is no unassailable evidence that the preservatives/antioxidants pose any serious health risks, many people are wary of their potential health risks and in general seek to avoid compositions which contain them. This can become a problem if they are present in nail antifungals since the patient may be reluctant to use the nail antifungal with the frequency required to eliminate the fungal infection.

Another disadvantage of antifungal formulations containing high amounts of oils or fats is that they leave a deposit on the nail surface which can be unpleasant for the user, and can also result in poor adherence of nail polish or the like to the nail surface. While this is a cosmetic issue, it is nonetheless a nuisance.

SUMMARY OF THE INVENTION

In one aspect, the present invention relates to a method for the topical treatment of nails.

In another aspect, the present invention relates to a method for treating nail fungus.

In yet another aspect, the present invention relates to a method for treating nail fungus using a composition which requires no preservatives or antioxidants for stability.

In yet a further aspect, the present invention relates to a topical treatment of nails with a composition which uses a minor amount of oil having a high oxidative stability index.

These and further features and advantages of the present invention will become apparent from the following detailed description, wherein reference is made to the figures in the accompanying drawings.

DETAILED DESCRIPTION OF PREFERRED EMBODIMENTS

As used herein, the terms "nail" or "nails" means one or more of the toe nails and/or finger nails of an animal, particularly humans.

The basic composition used in the method of the present invention comprises a urea-based component, a monohydric alcohol, a diol, undecylenic acid, a carboxylic acid other than undecylenic acid, dimethyl isosorbide, and O-2-naphthyl methyl(3-methylphenyl)thiocarbamate (tolnaftate).

Although the preferred urea-based component is urea itself, a urea-based component can comprise urea peroxide or carbamide peroxide. It is known that these urea-based components serve a cosmetic function in that they improve the visual appearance of the nail thereby providing an incentive for the user to be diligent in applying the composition, a necessity to eradicate fungal infections. Urea-based components also act as a nail penetrator and/or softener. The urea component will be present in the composition in an amount of from about 2 to about 15% by weight, preferably from about 2 to about 6% by weight, where all percentages are by weight of the total composition.

In addition to the urea-based component, the compositions used in the method of the present invention comprise a monohydric alcohol containing from 2 to 4 carbon atoms, the alcohol being present in an amount of from about 10 to about 55% by weight, preferably from about 15 to about 30% by weight. The monohydric alcohol can be ethanol, propanol, isopropanol, etc., isopropanol being preferred. Optionally, the composition can contain up to about 7% water.

Compositions used in the method of the present invention also contain a carboxylic acid component. Generally speaking, the carboxylic acid component comprises a C1 to C10 acid which can be alone and/or in an aqueous solution and is present in the composition in an amount of from about 10 to 25% by weight, preferably from about 10 to 15% by weight. Non-limiting examples of C1-C10 carboxylic acids suitable for use in the composition of the present invention include saturated and/or unsaturated, linear and/or branched, aliphatic mono-, di-, carboxylic acids, alkylaryl or aromatic dicarboxylic acids, oxy- and hydroxyl-carboxylic acids (e.g., alpha-hydroxy acids). Preferred carboxylic acids include formic acid, acetic acid, propionic acid, butyric acid, valeric acid, caproic acid, capyric acid, capric acid, sorbic acid, oxalic acid, hydroxybutyric acid, hydroxypropionic acids, lactic acid, glycolic acid, citric acid, malic acid, tartaric acid, malonic acid, fumaric acid, succinic acid, glutaric acid, apidic acid, pimelic acid, oxalacetic acid, phthalic acid, tartronic acid, pyruvic acid, and mixtures thereof. An especially preferred carboxylic acid is lactic acid.

The compositions used in the method of the present invention can also contain from about 2 to about 10% by weight, preferably from about 2 to about 6% by weight, of a carboxylic acid ester having the formula:

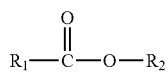

I wherein $R_1$ comprises 1 to 3 carbon atoms, and $R_2$ comprises 2 to 4 carbon atoms. Non-limiting suitable ester examples include methyl acetate, ethyl acetate, methyl propionate, etc., ethyl acetate being preferred.

One of the primary ingredients used in the compositions of the present invention is undecylenic acid (undec-10-enoic acid), an unsaturated fatty acid. While not wanting to be bound by any particular theory, it is believed that undecylenic acid acts as an emulsifier and also perhaps as a linking agent which brings certain components of the composition of the present invention together to form a clear, stable solution. It is also believed that undecylenic acid can act as a biocide/antimicrobial to some extent and thereby enhance the stability of the compositions of the present invention. Undeclyenic acid has the additional benefit that, in and of itself, it possesses antifungal properties thereby enhancing the efficacy of the compositions of the present invention in treating fungus as well as other nail infections. The undecylenic acid will be present in the composition of the present invention in an amount of from about 15 to about 30% by weight, preferably from about 20 to about 30% by weight.

The antifungal in the composition used in the method of the present invention is tolnaftate. The tolnaftate will generally be present in the composition in an amount of from about 0.3 to about 5% by weight, preferably from about 0.3 to about 3% by weight.

In addition to the above components, the antifungal compositions used in the method of the present invention can include other components which can function in one of several ways such as imparting solubility to render the composition a stable solution, imparting therapeutic benefits, imparting aesthetic effects or enhancing ease of application of the composition to the nails. Advantageously, and especially desirable as a solvent for use in the compositions used in the method of the present invention, is dimethyl isosorbide (DMI). The DMI will be present in the composition used in the method of the present invention in an amount of from about 8 to about 20% by weight.

One of the additional components that can be employed in the composition used in the method of the present invention is an ester of a fatty acid. Specifically, the fatty acid esters can have the formula:

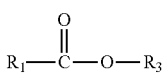

II wherein $R_3$ comprises 10 to 22 carbon atoms.

Non-limiting examples of suitable fatty acid esters are esters of caprylic acid, capric acid, lauric acid, myristic acid, palmitic acid, stearic acid, arachidic acid, and behenic acid. In particular, the ethyl, methyl, propyl, and/or isopropyl esters of these fatty acids can be employed, a preferred fatty acid ester being isopropyl myristate. When employed, the fatty acid ester will be present in an amount of from about 2 to about 10% by weight, preferably from about 2 to about 6% by weight.

To ensure mutual solubility of the components and enhance stability, the composition used in the method of the present invention can also include a diol containing from about 2 to about 4 carbon atoms. Non-limiting examples of suitable diols include ethylene glycol, propylene glycol, etc. A preferred diol is propylene glycol. The diol will generally be present in an amount of from about 4 to about 15% by weight, preferably from about 4 to about 10% by weight.

The compositions used in the method of the present invention, can also include with advantage jojoba oil. Jojoba oil is comprised mostly of free fatty acids and is characterized by its long shelf life as compared to other vegetable oils, primarily because it has no triglycerides. In this regard, it has an oxidative stability index of 60 as determined by AOCS standard method CD12b-92. When used, the jojoba oil will be present in the composition in an amount of from about 1 to about 10% by weight, preferably from about 1 to about 5% by weight.

Advantageously, the compositions used in the method of the present invention can contain vitamin E in an amount of from about 0.5 to about 10% by weight, preferably from about 0.5 to about 3% by weight. A desired form of vitamin E is vitamin E acetate having the formula $C_{31}H_{52}O_3$. Vitamin E acetate is commonly referred to as tocopherol acetate and is also known as DL-α-Tocoferil Acetate; (+/−)-α-Tocopherol Acetate; and DL-α-Tocopheryl Acetate. Vitamin E suitable for use in the compositions used in the method of the present invention is available from Spectrum Chemical Manufacture Corp. under the product code VI140, product name Vitamin E Acetate, USP.

A composition especially useful in the method of the present invention is one consisting essentially of 0.5 to 3% by weight tolnaftate, 2 to 6% by weight urea, 10 to 15% by weight lactic acid, 2 to 30% by weight undecylenic acid, 8 to 20% by weight DMI, 4 to 15% by weight propylene glycol, and 15 to 50% by weight isopropyl alcohol. This formulation, when used in the method of the present invention, showed the ability to rapidly eliminate fungal infections in toe nails.

The method of the present invention is used by applying the antifungal compositions disclosed herein to the nail(s). The term "applying" refers to any method of physically transferring the antifungal compositions used in the method of the present invention to the nail and if necessary, the surrounding skin. Such methods include but are not limited to, painting the compositions on the surface of the nail; spraying formulations containing the antifungal compositions on the nails using a spray pump; and combining the compositions of the present invention with a propellant so that it can be applied to the nails as an aerosol. Typically, for the treatment of nail diseases such as fungal infections, the method of the present invention is carried out by applying the composition once or twice per day, depending upon the intensity and resilience of the fungal infection. The method of the present invention can be used to treat diseases such as fungal diseases, bacterial diseases, and psoriasis. Fungal diseases of the human nail which can be treated in accordance with the method of the present invention include but are not limited to onychomychosis.

To further demonstrate the invention, the following non-limiting examples are presented:

Example 1

An antifungal composition was prepared which contained about 1.06 wt % tolnaftate, about 4.76 wt % ethyl acetate, about 4.51 wt % isopropyl myristate, about 3.18 wt % urea, about 21.67 wt % isopropyl alcohol, about 2.74 wt % jojoba oil, about 1.01 wt % vitamin E, about 6.61 wt % propylene glycol, about 12.80 wt % lactic acid, about 24.17 wt % undecylenic acid, about 12.19 wt % dimethyl isosorbide, and about 5.30 wt % purified water. The thus prepared antifungal composition was painted on the nails of two patients suffering severe toenail fungus. Markedly visible results in terms of reduced discoloration were seen in as little as ten days with respect to both patients. Additionally, after four weeks of treatment, it was found that there was marked elimination of the fungal infection in the toenails of both patients.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A method of treating diseases infecting nails, comprising:
   topically applying to said nails a composition comprising:
   from about 2 to about 15% by weight of a urea-based component;
   from about 10 to about 55% by weight of a monohydric alcohol containing 2 to 4 carbon atoms;
   from about 8 to about 20% by weight dimethyl isosorbide;
   from about 15 to about 30% by weight of undecylenic acid;
   from about 10 to about 25% by weight of a carboxylic acid component other than undecylenic acid;
   from about 0.3 to about 5% by weight of O-2-naphthyl methyl(3-methylphenyl) thiocarbamate; and
   from about 4 to about 15% by weight of a diol containing 2 to 4 carbon atoms.

2. The method of claim 1, wherein the composition further comprises:
   from about 1 to about 10% by weight jojoba oil.

3. The method of claim 1, wherein the composition further comprises:
   from about 0.5 to about 10% by weight Vitamin E.

4. The method of claim 1, wherein the composition further comprises:
   from about 2 to about 10% by weight of a carboxylic acid ester having the formula:

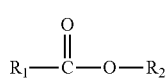

I wherein $R_1$ comprises 1 to 3 carbon atoms, and $R_2$ comprises 2 to 4 carbon atoms.

5. The method of claim 1, wherein the composition further comprises:
   from about 2 to about 10% by weight of a fatty acid ester having the formula

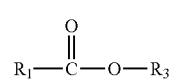

II wherein $R_1$ comprises 1 to 3 carbon atoms, and $R_3$ comprises 10 to 22 carbon atoms.

6. The method of claim 1, wherein said urea-based component is present in an amount of from about 2 to about 6% by weight, said monohydric alcohol is present in an amount of from about 15 to about 30% by weight, said carboxylic acid component is present in an amount of from about 10 to about 15% by weight, said undecylenic acid is present in an amount of from about 20 to about 30% by weight, said dimethyl isosorbide is present in an amount of from about 8 to about 20% by weight, and said O-2-naphthyl methyl(3-methylphenyl)thiocarbamate is present in an amount for from about 0.3 to about 3% by weight.

7. The method of claim 1, wherein said urea-based component comprises urea.

8. The method of claim 1, wherein said monohydric alcohol comprises isopropyl alcohol.

9. The method of claim 1, wherein said carboxylic acid component is selected from the group consisting of formic acid, acetic acid, propionic acid, butyric acid, valeric acid, caproic acid, capyric acid, capric acid, sorbic acid, oxalic acid, hydroxybutyric acid, hydroxypropionic acids, lactic acid, glycolic acid, citric acid, malic acid, tartaric acid, malonic acid, fumaric acid, succinic acid, glutaric acid, apidic acid, pimelic acid, oxalacetic acid, phthalic acid, tartronic acid, pyruvic acid, and mixtures thereof.

10. The method of claim 9, wherein said carboxylic acid comprises lactic acid.

11. The method of claim 5, wherein said fatty acid ester comprises isopropyl myristate in an amount of from about 2 to about 10% by weight.

12. The method of claim 1, wherein said diol comprises propylene glycol in an amount of from about 4 to about 15% by weight.

13. The method of claim 1, wherein applying said composition to the nails comprises painting said composition on said nails.

14. The method of claim 1, wherein applying said composition to the nails comprises spraying said composition on said nails.

* * * * *